United States Patent [19]
Ohno et al.

[11] Patent Number: 5,598,451
[45] Date of Patent: Jan. 28, 1997

[54] APPARATUS FOR MEASURING THE SULFUR COMPONENT CONTAINED IN OIL

[75] Inventors: Kazunaga Ohno; Yukio Hashizume; Kazuo Husimi; Masahiko Kuwata, all of Tokyo, Japan

[73] Assignee: DKK Corporation, Tokyo, Japan

[21] Appl. No.: 551,823

[22] Filed: Nov. 7, 1995

[30] Foreign Application Priority Data

Nov. 11, 1994 [JP] Japan .................................. 6-301626

[51] Int. Cl.⁶ .................................................. G01N 23/223
[52] U.S. Cl. ........................... 378/44; 378/45; 378/47
[58] Field of Search .............................. 378/44, 45, 47, 378/48, 51, 52, 56, 53

[56] References Cited

U.S. PATENT DOCUMENTS 4,037,099  7/1977  Oda et al. ................................. 378/47
4,577,338  3/1986  Takahashi et al. ....................... 378/207
5,107,527  4/1992  Heikki et al. ............................ 378/47

FOREIGN PATENT DOCUMENTS 6128859  12/1986  Japan .

OTHER PUBLICATIONS

F. S. Goulding and J. M. Jaklevic, "XRF Analysis—Some Sensitivity Comparisons Between Charged-Particle and Photon Excitation", Nuclear Instruments And Methods, pp. 323–332, 1977.

Primary Examiner—Don Wong
Attorney, Agent, or Firm—Klaus J. Bach

[57] ABSTRACT

An apparatus for measuring the Sulfur component contained in oil includes an X-ray tube having a target made of Titanium or Scandium, a filter made of Titanium or Scandium for filtering said X-ray radiated from the X-ray tube, a measurement cell for introducing a sample to be measured therein, and a detector for detecting fluorescent X-rays radiated from the sample. According to the invention, the X-ray tube has a target made of Titanium or Scandium and the X-rays generated from the X-ray tube are filtered by the filter, which is made of Titanium or Scandium, so that the background of the X-rays for the measurement against the fluorescent X-rays of the Sulfur is reduced and therefore even a small amount of Sulfur contained in the sample can be correctly detected.

6 Claims, 6 Drawing Sheets

FIG_5
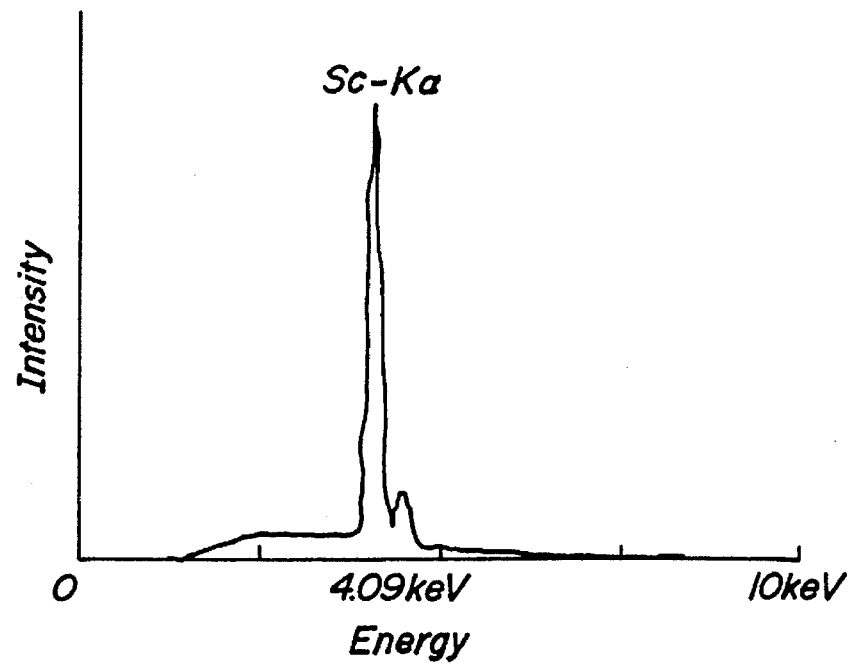
FIG_6
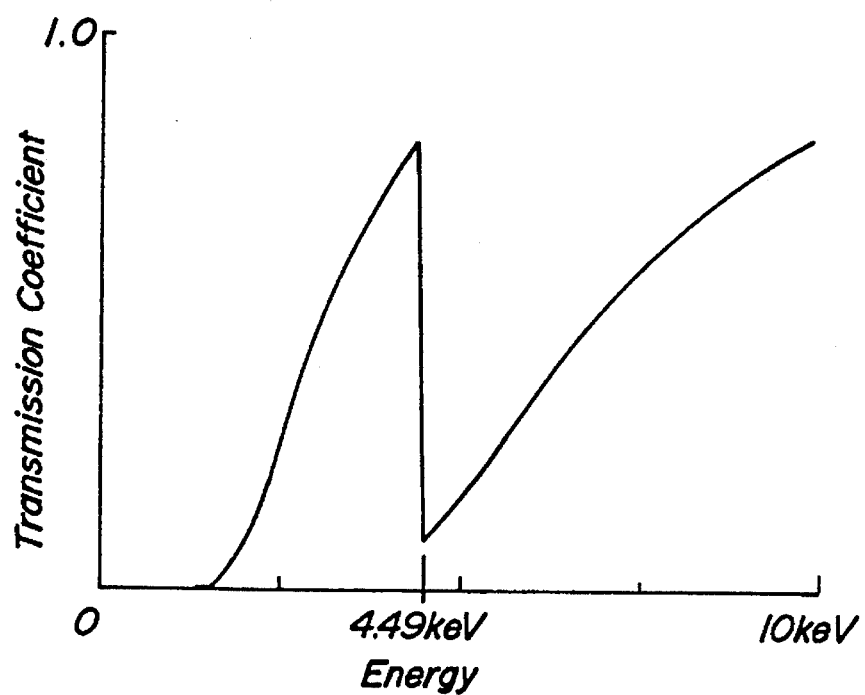

FIG_7
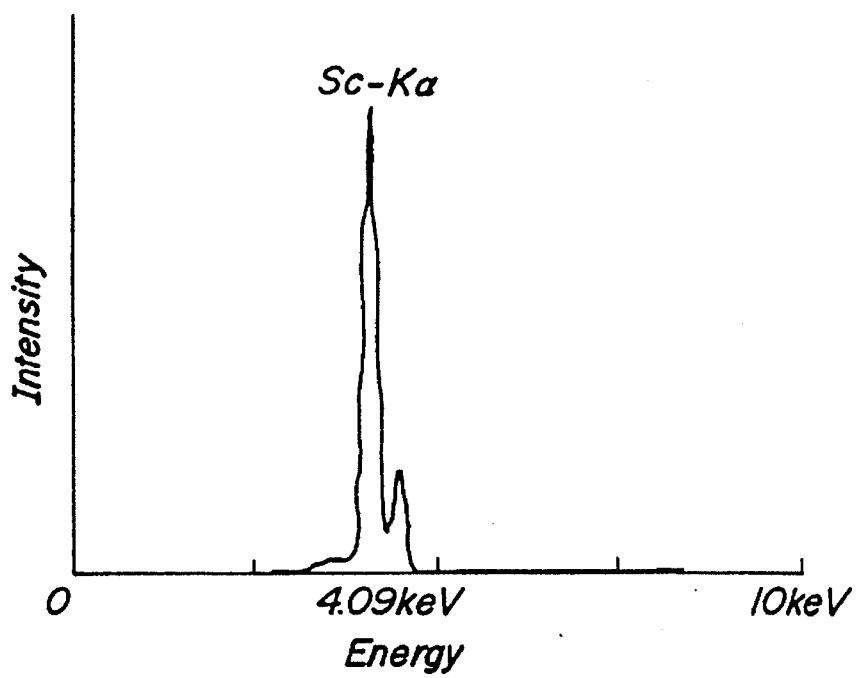
FIG_8
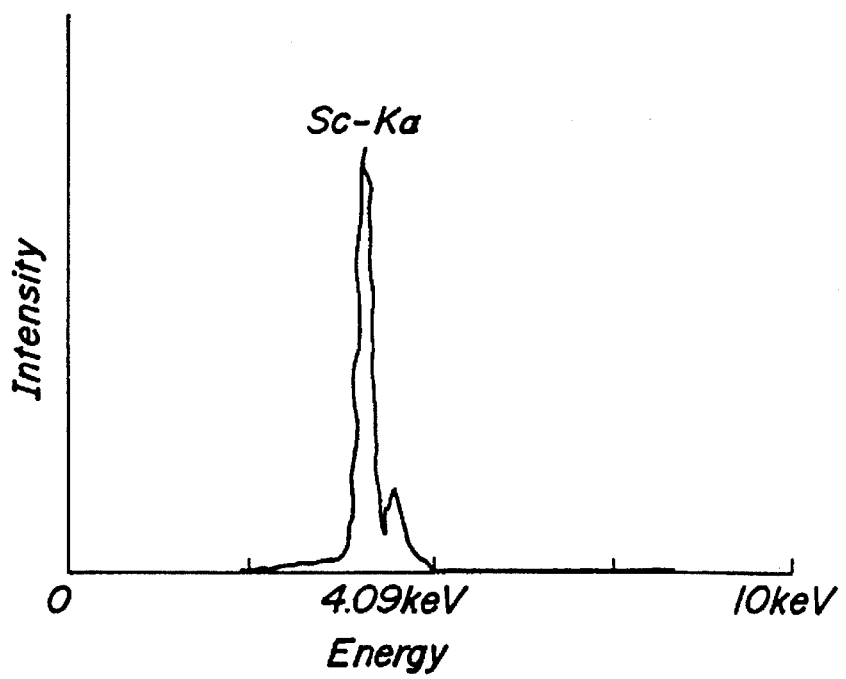

FIG_9
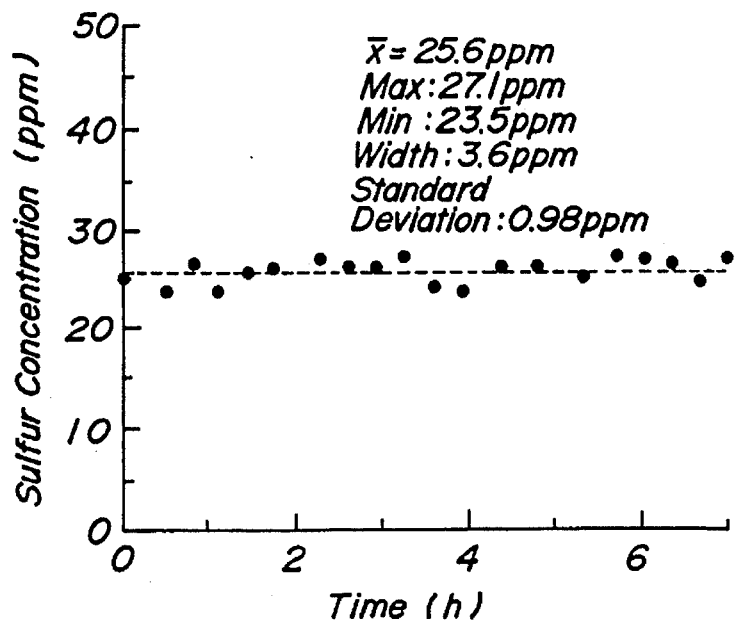
FIG_10
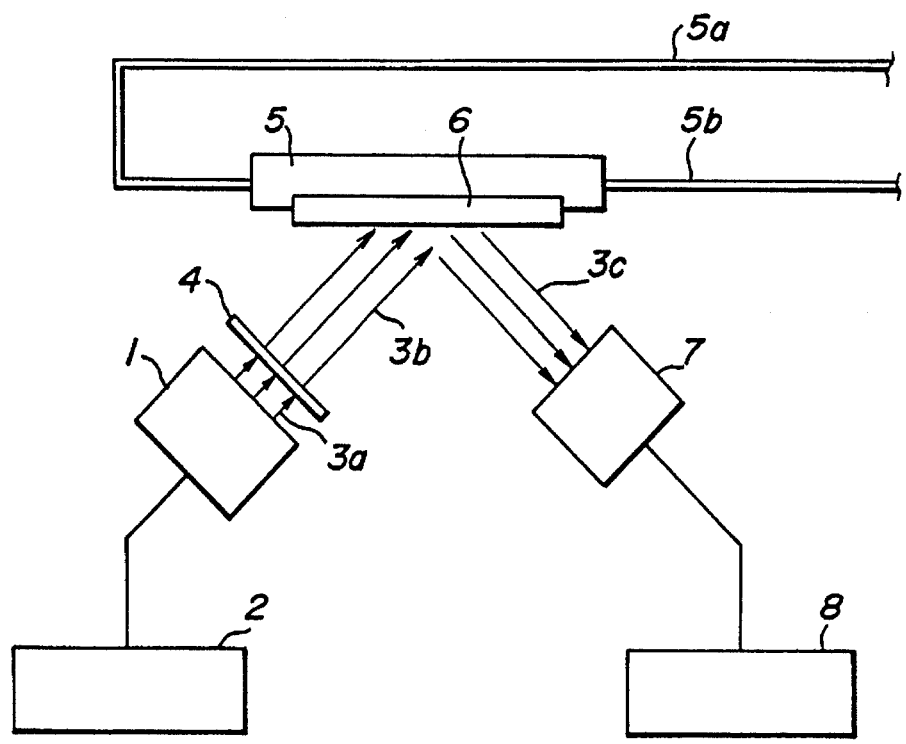

5,598,451

APPARATUS FOR MEASURING THE SULFUR COMPONENT CONTAINED IN OIL

BACKGROUND OF THE INVENTION

1) Field of the Invention

The present invention relates to an apparatus for measuring the Sulfur component contained in oil. Particularly, the invention relates to an apparatus for measuring the concentration of the Sulfur component contained in oil products such as kerosene and gasoline, and raw material of oil such as crude petroleum, or intermediate products thereof.

2) Related Art

Crude petroleum, the raw material of oil products, contains some Sulfur components; also kerosene and gasoline, which are refined products of crude petroleum, contain small amounts of Sulfur component therein. Since an allowable upper limit of the Sulfur component contained in the refined products of oil is determined by standards according to each country, it is important to measure the concentration of the Sulfur component contained in such products during or after refining the crude petroleum in order to manage or control the concentration of said Sulfur component.

There are previously known many methods for measuring the Sulfur component contained in the refined products of crude petroleum or in the refined products of oil, such as a micro coulometric titration oxidation method, an X-ray absorption method, a wavelength dispersive X-ray fluorescent analyzing system (WDS), or an energy dispersive X-ray fluorescent analyzing system(EDS).

Out of these conventional methods, a direct excitation type energy dispersive X-ray fluorescent analyzing system was well developed. According to this system, X-rays are directly applied onto a sample without changing the X-rays into monochrometric X-rays with the aid of a monochrometer, so that the sulfur component contained in oil can be easily measured on the spot, such as an oil factory, without applying any pre-operation to the sample; and it is not necessary to make the size of the apparatus large and the construction complex.

However, this type of system has a drawback in that it has a low measurement accuracy, which does not meet with the recent requirements in the measurement of the Sulfur component in oil. Therefore, it has been desired for a long time to develop an apparatus for measuring the Sulfur component contained in oil by which the Sulfur component can be measured with high accuracy.

The reason why a sufficient measurement accuracy cannot be obtained in the conventional direct excitation type energy dispersive X-ray fluorescent analyzing system will be explained below, referring to an apparatus where Molybdenum is used as a material of the target for the X-ray tube thereof. FIG. 1 shows a spectrum of energy of an X-ray radiated from the X-ray tube in which Molybdenum is used as a material of the target thereof. In FIG. 1, the energy of the X-rays radiated from the X-ray tube is taken on a horizontal axis and an intensity (brightness) thereof on a vertical axis. As shown in FIG. 1, the spectrum of the X-ray radiated from the X-ray tube is determined by a voltage for accelerating electronic beams to be applied on the target and the material of the target. When the electronic beams hit the target, characteristic X-rays of the material of the target and continuous X-rays (white X-rays) are generated from the X-ray tube. When the analysis is conducted using fluorescent X-rays, such characteristic X-rays are applied to the sample to excite an objective substance to be measured; and then fluorescent X-rays (characteristic X-rays) radiated from the objective substance are detected to know the concentration of the objective substance contained in the sample. In order to excite the objective substance in the measurement, it is necessary to apply X-rays having a greater energy than that of the objective substance in the measurement at an X-ray absorption edge thereof.

In the case that the objective substance to be measured is Sulfur, the energy at an X-ray absorption edge of the K-shell of a Sulfur atom is 2.47 keV. It is well known that if white X-rays having a peak energy of about 4.5–5 keV are applied on the Sulfur atom, the characteristic X-rays radiated from the K-shell of the Sulfur atom are excited in an effective manner. In the conventional measurement apparatus, however, the white X-rays used for exciting the characteristic X-rays have a considerably greater energy width, as shown in FIG. 1, when the electronic beams are accelerated at a voltage of 10 kV, for instance. That means during the period when the electronic beams are applied on the target, the energy around 2.31 keV, i.e. the energy of the K-shell characteristic X-rays of the Sulfur atom, is also radiated from the target, being included in the white X-rays. Therefore, when the white X-rays are applied on the sample oil, X-rays are scattered by the sample, and the scattered sample includes the K-shell characteristic X-rays of the Sulfur atoms; and such X-rays become a large background against the characteristic X-rays to be measured. Thus, if the concentration of the Sulfur component contained in the sample is low, it is difficult to measure it correctly. For instance, when the concentration of Sulfur component to be measured is several tens ppm, a large fluctuation of about 10 ppm is generated, working as the background.

That is to say, since radiations are generated as a probability phenomenon during the period when X-rays are measured (radiations are measured), a fluctuation would statistically appear in the measurement values. Therefore, if the background component is great, the background per se would statistically have a fluctuation; and if the signal generated from the objective substance to be measured is not sufficiently greater than the width of the fluctuation of the background, the signal to be detected would be varied in the fluctuation of the background. As stated above, in the conventional apparatus, when the signal obtained from the objective substance to be measured is small, it is difficult to measure the substance correctly. Therefore, in order to correctly measure a very small amount of a component contained in the sample, it is necessary to reduce the background as much as possible.

SUMMARY OF THE INVENTION

The purpose of the present invention is to provide an apparatus for measuring the Sulfur component contained in oil using an energy dispersive X-ray fluorescent analyzing system, where the Sulfur component contained in oil can be correctly measured even if the concentration of the Sulfur component contained in oil is very low. It should be noted that the term of "oil" includes all of oil products such as kerosene and gasoline, and raw material of oil such as crude petroleum, or intermediate products thereof in this specification.

In order to solve the above mentioned drawbacks, the present invention has the following features. The first aspect of the present invention is that an apparatus for measuring the Sulfur component contained in oil comprises an X-ray tube having a target made of Titanium, a filtering means for filtering X-rays radiated from said X-ray tube comprising a filter made of Titanium; a measurement cell for introducing a sample to be measured therein; an X-ray applying means for applying X-rays filtered by said filtering means onto said sample to excite fluorescent X-rays from said sample; and a detecting means for detecting said fluorescent X-rays excited from said sample.

The present invention has its second aspect that an apparatus for measuring the Sulfur component contained in oil comprises an X-ray tube having a target made of Scandium, a filtering means for filtering X-rays radiated from said X-ray tube comprising a filter made of Scandium; a measurement cell for introducing a sample to be measured therein; an X-ray applying means for applying X-rays filtered by said filtering means onto said sample to excite fluorescent X-rays from said sample; and a detecting means for detecting said fluorescent X-rays excited from said sample.

The present invention has its third aspect that an apparatus for measuring the Sulfur component contained in oil comprises an X-ray tube having a target made of Scandium, a filtering means for filtering X-rays radiated from said X-ray tube comprising a filter made of Titanium; a measurement cell for introducing a sample to be measured therein; an X-ray applying means for applying X-rays filtered by said filtering means onto said sample to excite fluorescent X-rays from said sample; and a detecting means for detecting said fluorescent X-rays excited from said sample.

According to the first aspect of the present invention, Titanium is used for a material of the target of the X-ray tube and a primary filter made of Titanium foil is provided between the X-ray tube and the measurement cell. FIG. 2 is a graph showing a spectrum of an X-ray generated from the X-ray tube having a target made of Titanium; and FIG. 3 is a graph representing an X-ray transmission characteristic of a filter made of Titanium foil. As shown in FIG. 2, X-rays including strong characteristic X-rays radiated from the K-shell of Titanium in their spectra are generated from the X-ray tube by using Titanium as a material of the target; and, by filtering the thus obtained X-rays, whose energy is 4.51 keV, by the Titanium filter, exciting X-rays having a spectrum where the intensity of the characteristic X-rays of Titanium is multiplied by the X-ray transmission coefficient as shown in FIG. 3, are applied on the sample in the measurement cell. The spectrum of this exciting X-ray is shown in FIG. 4.

As apparent from FIG. 4, the exciting X-rays being applied to the sample of the measurement cell in the apparatus according to the present invention include strong X-rays having an energy necessary for exciting Sulfur atoms in the sample but almost no X-ray having an energy around 2.31 keV, which corresponds to the energy of the K-shell characteristic X-rays of the Sulfur. That is to say, the energy of the exciting X-rays has a characteristic that is strong around 4.51 keV, which corresponds to the K-shell characteristic X-rays of Titanium, with a narrow width thereof. By applying such exciting X-rays onto the sample to be measured, the Sulfur atoms in the sample can be sufficiently excited and the background against the K-shell characteristic X-rays of the Sulfur can be reduced. Therefore, even if the amount of the Sulfur component contained in the sample is very small, it is possible to detect it in a correct manner.

It should be noted that Scandium may also be used as a material of the target of the X-ray tube instead of Titanium. In the second aspect of the present invention, Scandium is used as the material of the target of the X-ray tube and the X-rays generated from the tube are filtered by a filter made of Scandium. In such a case, almost the same effect as that of the first aspect of the invention can be obtained. FIG. 5 is a graph showing a spectrum of an X-ray generated from the X-ray tube having a Scandium target; FIG. 6 is a graph illustrating a transmission characteristic for X-rays in the filter made of Scandium; and FIG. 7 is a graph depicting a spectrum of exciting X-ray which is obtained in an apparatus constructed such that the X-rays are generated from the X-ray tube having a Scandium target and the thus generated X-rays are filtered by the Scandium filter. As depicted in FIG. 7, the excited X-rays include strong X-rays having a sufficient energy necessary for exciting the Sulfur atoms in the sample to be measured but almost no X-ray having an energy around 2.31 keV, which corresponds to the energy of the K-shell characteristic X-rays of the Sulfur.

The third aspect of the present invention has an aspect such that the X-ray tube has a target made of Scandium and X-rays generated by the X-ray tube are filtered by a filter made of Titanium. FIG. 8 is a graph showing a spectrum of an exciting X-ray obtained in the apparatus according to the third aspect of the invention. As shown in FIG. 8, the exciting X-rays also include strong X-rays having an energy necessary for exciting the Sulfur atoms in the sample to be measured, but almost no X-ray component having an energy of about 2.31 keV, which corresponds to the energy of the K-shell characteristic X-rays of the Sulfur. Therefore, according to the third aspect of the present invention, the Sulfur atoms in the sample to be measured can be sufficiently excited and the background against the K-shell characteristic X-rays of the Sulfur being made incident upon the detecting means can be reduced.

BRIEF EXPLANATION OF DRAWINGS

FIG. 5 is a graph showing a spectrum of an X-ray radiated from an X-ray tube having a target made of Scandium;

FIG. 6 is a graph depicting the X-ray transmission characteristic of a filter made of Scandium;

FIG. 7 is a graph illustrating a spectrum of an exciting X-ray which is radiated from an X-ray tube having a Scandium target and then filtered by a Scandium filter;

FIG. 8 is a graph representing a spectrum of an exciting X-ray which is radiated from an X-ray tube having a Scandium target and then filtered by a Titanium filter;

FIG. 9 is a graph showing a condition of the fluctuation in the measurement result when the Sulfur component contained in a sample is continuously measured;

FIG. 10 is a schematic view illustrating a construction of an apparatus for measuring the Sulfur component contained in oil according to the present invention.

DETAILED EXPLANATION OF THE PREFERRED EMBODIMENTS

Figure 1:
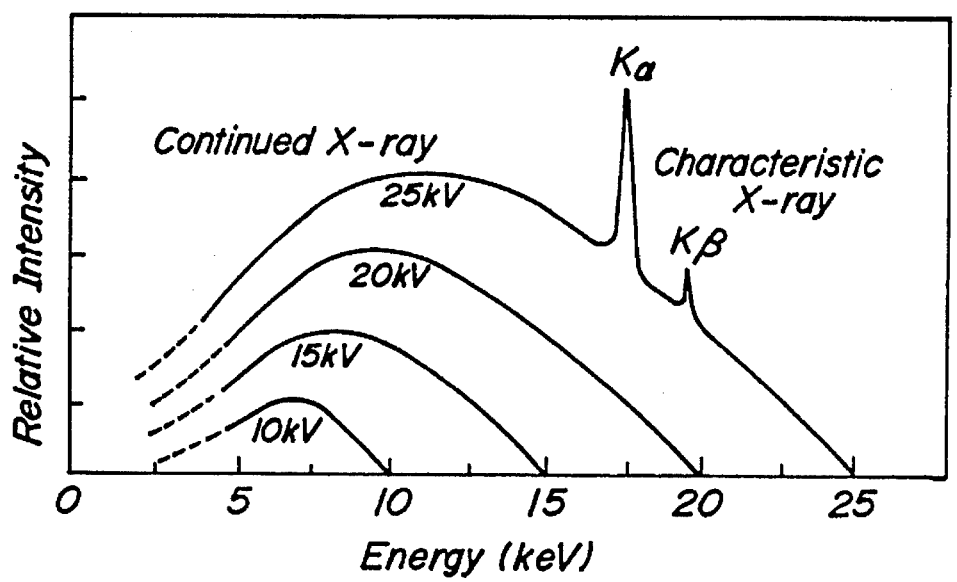
FIG. 1 is a graph showing a spectrum of an X-ray radiated from an X-ray tube having a target made of Molybdenum.

The preferred embodiments according to the present invention will be explained below, referring to the drawings.

FIG. 10 is a schematic view showing a construction of an apparatus for measuring the Sulfur component contained in oil according to the present invention. In FIG. 10, the numerical reference 1 represents an X-ray tube, 2 a high-voltage power supply for use in generating X-rays, 3 X-rays, 4 a filter, 5 a sample cell, 6 an X-ray window provided on the sample cell 7 an X-ray detector, and the numerical number 8 represents a measurement circuit. The X-ray tube 1 is driven by the high-voltage power supply 2 for use in generating X-rays and the X-rays 3a are generated from the X-ray tube 1. The X-rays 3a are filtered to become X rays 3b by the filter 4 which is located between the X-ray tube 1 and the sample cell 5; and then the X-rays 3b are made incident upon the X-ray window 6 which is provided on the sample cell 5. The sample cell 5 comprises a sample inlet 5a and a sample outlet 5b through which the sample to be measured flows; and the X-rays 3b are applied upon the sample via the X-ray window 6. Then, X-rays 3c used for the measurement including both fluorescent X-rays radiated from the Sulfur component contained in the sample and X-rays scattered by carbon atoms, etc. in the sample are made incident upon the X-ray detector 7. The detector 7 detects the fluorescent X-rays radiated from the Sulfur component contained in the sample to supply a detection signal to the measurement circuit 8, where the detection signals are measured to obtain a concentration of the Sulfur component.

Figure 2:
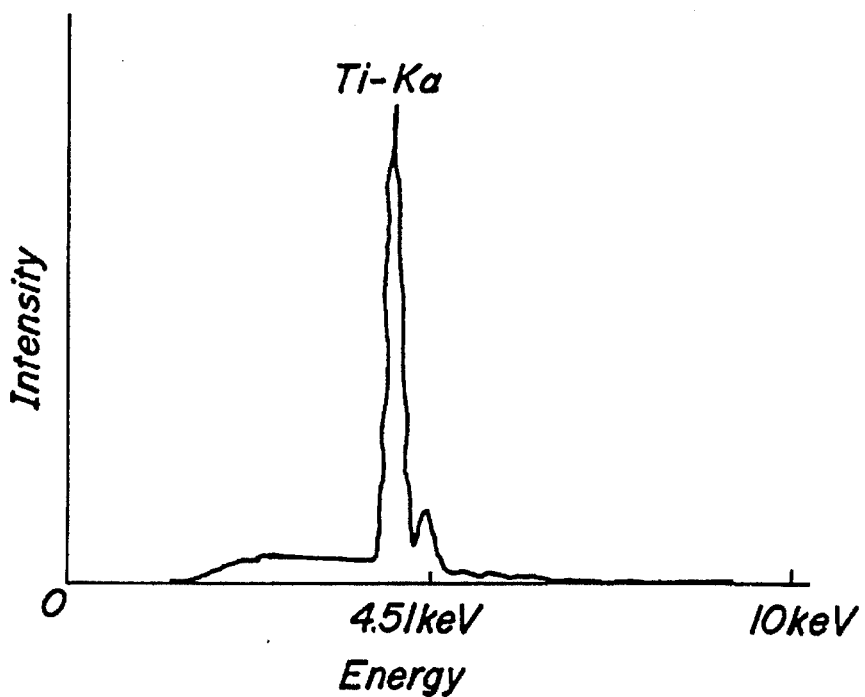
FIG. 2 is a graph depicting a spectrum of an X-ray radiated from an X-ray tube having a target made of Titanium.
Figure 3:
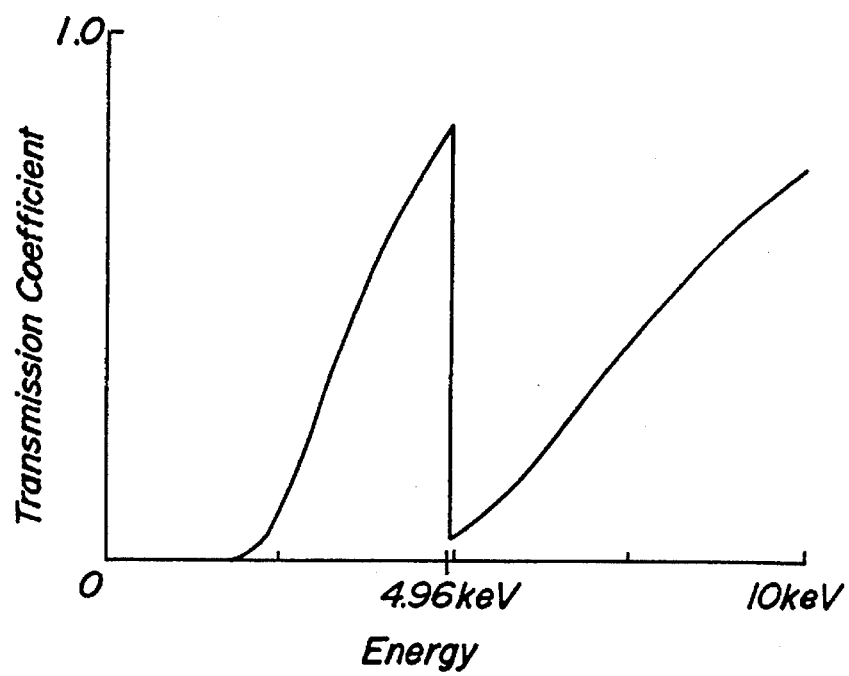
FIG. 3 is a graph illustrating an X-ray transmission characteristic of a filter made of Titanium.
Figure 4:
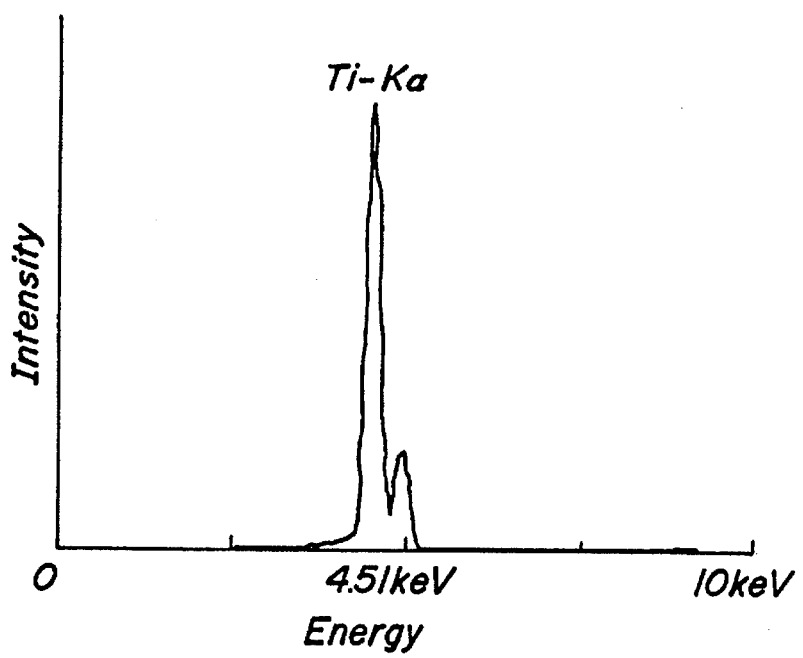
FIG. 4 is a graph representing a spectrum of an exciting X-ray which is radiated from the X-ray tube having a Titanium target and then filtered by a Titanium filter.

In the apparatus for detecting the Sulfur component contained in oil according to the first embodiment of the present invention, the X-ray tube 1 comprises a target made of Titanium (not shown). When driving the X-ray tube 1 with a comparatively low accelerating voltage, the white X-rays 3a including strong K-shell characteristic X-rays of Titanium (4.51 keV) as shown in FIG. 2 are generated. The X-rays 3a are then filtered by a primary X-ray filter 4 which is made of Titanium foil. By the filtering, exciting X-rays 3b, whose spectrum is as shown in FIG. 4, having strong K-shell characteristic X-rays of Titanium with a small width of their energy are obtained. The X-rays 3b are applied to the sample flowing through the sample cell 5 via the X-ray window 6. It should be noted that the window 6 is made of Beryllium.

Figure 11:
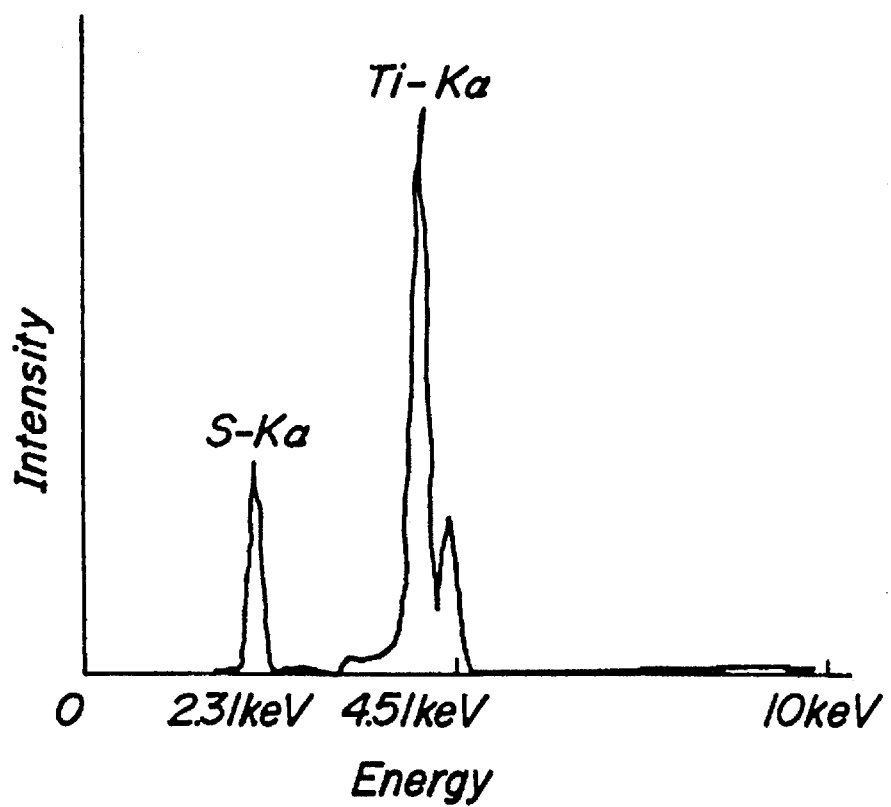
FIG. 11 is a graph representing a spectrum of an X-ray used for the measurement of the Sulfur component in the apparatus according to the first embodiment of the present invention.

When the X-rays 3b are applied to the sample, the Sulfur atoms contained in the sample are exited by the exciting X-rays 3b, and X-rays having an energy of 2.31 keV, i.e. the K-shell characteristic of the Sulfur, are radiated from the Sulfur atoms. Additionally, the X-rays 3b are scattered by the carbon atoms, etc., contained in the sample, so that X-rays 3c, which are used for the measurement, containing both the shell-K characteristic X-rays of the Sulfur and the X-rays scattered by the Carbon atoms, etc. are made incident upon the detector 7. FIG. 11 shows a spectrum of the X-ray 3c for the measurement. As shown in FIG. 11, the X-rays 3c used for the measurement include fluorescent X-rays which are radiated from the Sulfur atoms contained in the sample but the background component is reduced. In the measurement apparatus according to the present invention, the background can be reduced down to about 100 ppm, when it is converted into the concentration of Sulfur. In this case, the fluctuation $\sigma$ (standard deviation) of the measurement value of the Sulfur component becomes very small, i.e. $1\sigma<1$ ppm, when the sample containing the Sulfur component at a concentration of 50 ppm is successively measured, so that the repeatability of the fluorescent X-rays of the Sulfur can be improved. FIG. 9 shows the fluctuation of the measurement value when the Sulfur component is measured under the above-mentioned condition.

It should be noted that a semiconductor detector is used as the detecting means 7, but other types of detector may be used as long as the detectors have an energy resolution capability. The fluorescent X-rays of the Sulfur contained in the X-rays 3c for the measurement are detected by the detector 7. The detected signal is then supplied to the measurement circuit 8, where the X-ray intensity is measured at every energy to detect a variation of the intensity of the K-shell characteristic X-rays of the Sulfur. The concentration in weight of the Sulfur component contained in the sample can be determined from this variation.

As stated in the above, according to the measurement apparatus of the first embodiment of the present invention, the X-rays 3a, which include the strong K-shell characteristic X-rays of Titanium, are generated by using Titanium as a material of the target of the X-ray tube in order to excite the Sulfur atoms in the sample in an effective manner: and the X-rays 3a generated from the X-ray tube are filtered by the primary X-ray filter, which is made of Titanium. Therefore, the X-rays 3c used for the measurement, where the background component against the K-shell characteristic X-rays of the Sulfur is reduced, can be obtained without loosing the intensity of the X-rays for exciting the Sulfur atoms. Thus, even if the amount of the sulfur component contained in the sample is very small, it is possible to correctly detect the Sulfur component without the influence or intereference of the background component.

FIGS. 5 and 7 are graphs showing the spectra of X-rays 3a generated from the X-ray tube 1 and X-rays 3b filtered by the filtering means in the apparatus according to the second embodiment of the present invention. In the second and third embodiments, the constructions of the apparatuses are the same as that of the first embodiment except for the material of the target provided in the X-ray tube and the material of the filter. Therefore, the same numerical references are given for the elements commonly used in the first to third embodiments and the explanation is therefore omitted here.

In the second embodiment, the target of the X-ray tube is made of Scandium and the white X-rays 3a generated from the tube have strong K-shell characteristic X-rays of Scandium. The white X-rays 3a are filtered by a filter made of Scandium in order to reduce the background component against the exciting X-rays of the Sulfur. As shown in FIG. 5, even when the target of the X-ray tube is made of Scandium, it is possible to obtain the X-rays 3a which have a sufficient energy to excite the Sulfur atoms contained in the sample. Further, since the X-rays 3a are filtered by the Scandium filter, the exciting X-rays which have the strong K-shell characteristic X-rays of Scandium (4.09 keV) but almost no X-ray having an energy corresponding to the energy of the K-shell characteristic X-ray of the Sulfur can be made incident upon the measurement cell 5. FIG. 6 shows a spectrum of such an exciting X-ray 3c.

In the third embodiment, Scandium is used as the material of the target of the X-ray tube 1; and the filter 4 made of Titanium is arranged between the X-ray tube 1 and the measurement cell 5 in order to reduce the background against the X-rays 3c used for the measurement, which is radiated from the sample in the sample cell 5. FIG. 8 is a spectrum of the X-ray 3b, which is obtained after being filtered by the Titanium filter 4, in the apparatus according to the third embodiment of the present invention. As stated in the above, even in the case that Scandium is used as the target material of the X-ray tube, it is possible to generate the X-rays 3a having a sufficient energy to excite the Sulfur atoms in the sample; and it is also possible to apply the exciting X-rays 3b, which have the strong K-shell characteristic X-rays of the Scandium (4.09 eV) but almost no X-ray having an energy corresponding to that of the K-shell characteristic X-ray of the Sulfur, on to the sample flowing through the measurement cell 5.

As is clear from the above explanation, the background component against the fluorescent X-rays of the Sulfur, which is contained in the X-rays 3c being radiated or scattered from the sample in the measurement cell 5, can also be reduced in the second and third embodiments. Therefore, according to the present invention, in the case that only a small amount of the Sulfur component is contained in the sample, it is possible to detect it with a high accuracy.

In the above explained embodiments, Titanium or Scandium is used as the material of the target provided in the X-ray tube and Titanium or Scandium is used as the material of the primary filter. However, it may be possible to use Vanadium instead of Titanium or Scandium. For instance, the combination of a Vanadium target and a Vanadium filter or the combination of a Titanium target and a Vanadium filter, etc. can be considered.

In the above-mentioned embodiments, the sample cell 5 is constructed such that the sample flows from the sample inlet 5a to the sample outlet 5b. However, the construction of the sample cell 5 is not limited to that of these embodiments. Further, it may be possible to arrange such that the X-rays are applied to the sample not via the X-ray window but directly. In this case, the X-ray window would be unnecessary.

As explained in detail, according to the present invention, the Sulfur component contained in oil can be measured with a high sensitivity. In addition, it is not necessary to apply any pre-conditioning to the sample to be measured. In other words, the Sulfur component can be detected without any action when the sample is introduced into the sample cell. Therefore, the apparatus according to the present invention can be put on the spot as a process meter. Further, the size of the apparatus as a whole can be made compact. Furthermore, nowhere does the temperature become high in the apparatus and no precision meter, such as a monochormeter, is used, also it is possible to use in places where the temperature becomes high and strong vibrations are generated.

What is claimed is:

1. An apparatus for measuring the Sulfur component contained in oil comprising:

an X-ray tube having a target made of Titanium;

a filtering means for filtering X-rays radiated from said X-ray tube comprising a filter made of Titanium;

a measurement cell for introducing a sample to be measured therein;

an X-ray applying means for applying X-rays filtered by said filtering means onto said sample in the measurement cell to emit fluorescent X-rays from said sample; and a detecting means for detecting said fluorescent X-rays emitted from said sample.

2. An apparatus for measuring the Sulfur component contained in oil comprising:

an X-ray tube having a target made of Scandium;

a filtering means for filtering X-rays radiated from said X-ray tube comprising a filter made of Scandium;

a measurement cell for introducing a sample to be measured therein;

an X-ray applying means for applying X-rays filtered by said filtering means onto said sample in the measurement cell to emit fluorescent X-rays from said sample; and a detecting means for detecting said fluorescent X-rays emitted from said sample.

3. An apparatus for measuring the Sulfur component contained in oil comprising:

an X-ray tube having a target made of Scandium;

a filtering means for filtering X-rays radiated from said X-ray tube comprising a filter made of Titanium;

a measurement cell for introducing a sample to be measured therein;

an X-ray applying means for applying X-rays filtered by said filtering means onto said sample in the measurement cell to emit fluorescent X-rays from said sample; and a detecting means for detecting said fluorescent X-rays emitted from said sample.

4. An apparatus for measuring the Sulfur component contained in oil according to claim 1, wherein:

said detecting means comprises a measurement circuit for measuring an intensity of said fluorescent X-rays at every energy level to detect a variation of K-shell characteristic X-rays of the Sulfur component contained in the sample.

5. An apparatus for measuring the Sulfur component contained in oil according to claim 2, wherein:

said detecting means comprises a measurement circuit for measuring an intensity of said fluorescent X-rays at every energy level to detect a variation of K-shell characteristic X-rays of the Sulfur component contained in the sample.

6. An apparatus for measuring the Sulfur component contained in oil according to claim 3, wherein:

said detecting means comprises a measurement circuit for measuring an intensity of said fluorescent X-rays at every energy level to detect a variation of K-shell characteristic X-rays of the Sulfur component contained in the sample.

* * * * *

UNITED STATES PATENT AND TRADEMARK OFFICE
CERTIFICATE OF CORRECTION

PATENT NO. : 5,598,451
DATED : January 28, 1997
INVENTOR(S) : Kazunaga Ohno, et al It is certified that error appears in the above-identified patent and that said Letters Patent is hereby corrected as shown below:

On the title page, item [73], add the following assignees:
JEOL LTD. and JEOL ENGINEERING CO., LTD.

Signed and Sealed this

Second Day of September, 1997

*Attest:*

BRUCE LEHMAN

*Attesting Officer*      *Commissioner of Patents and Trademarks*